Figure 1:
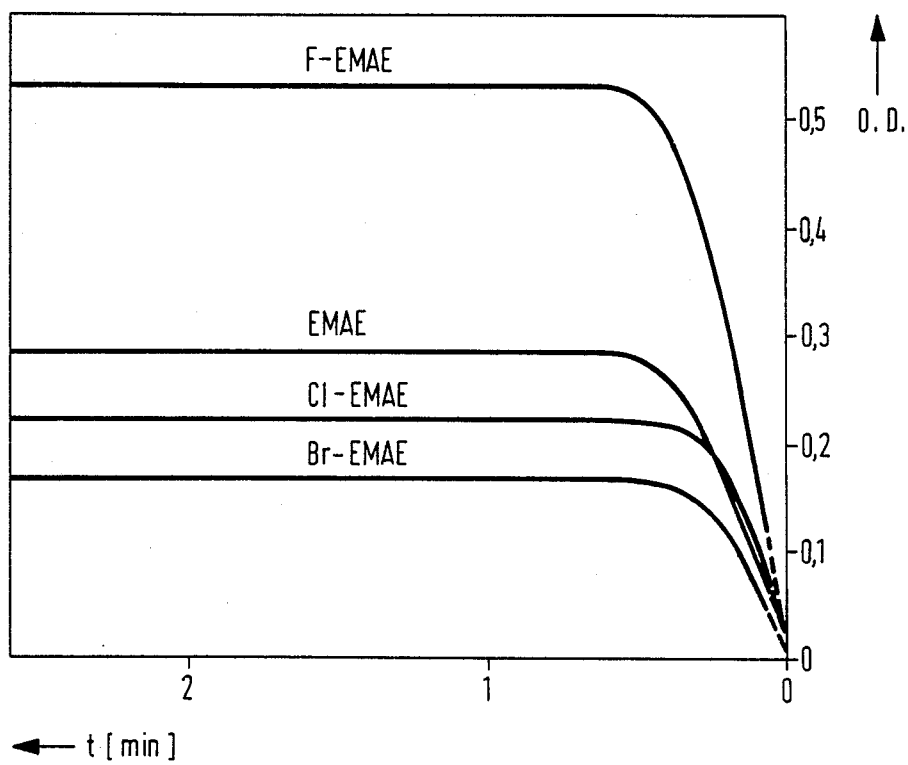

United States Patent [19]

Batz et al.

[11] Patent Number: 4,912,258
[45] Date of Patent: Mar. 27, 1990

[54] FLUORINATED ANILINE DERIVATIVES AND THEIR USE

[75] Inventors: Hans-Georg Batz, Tutzing; Rupert Herrmann, Weilheim, both of Fed. Rep. of Germany

[73] Assignee: Boehringer Mannheim GmbH, Mannheim, Fed. Rep. of Germany

[21] Appl. No.: 159,422

[22] Filed: Feb. 5, 1988

Related U.S. Application Data

[63] Continuation of Ser. No. 720,583, Apr. 8, 1985, abandoned.

[30] Foreign Application Priority Data

Apr. 11, 1984 [DE] Fed. Rep. of Germany ....... 3413693

[51] Int. Cl.$^4$ .................... C07C 103/44; C07C 87/52; C07C 87/60; C07C 87/14
[52] U.S. Cl. .................................. 564/153; 564/157; 564/220; 564/367; 564/374; 564/384; 564/442; 564/82; 564/99; 544/35; 544/51; 544/102; 544/104; 544/105; 544/347; 544/353; 546/93; 546/95; 546/166; 548/178; 548/179; 548/180; 548/152; 548/217; 548/324; 548/428; 540/477; 540/547; 540/552; 540/556; 540/581; 540/593; 8/408; 8/649
[58] Field of Search ............... 564/442, 367, 153, 157, 564/220, 374, 384

[56] References Cited

U.S. PATENT DOCUMENTS

| | | | |
|---|---|---|---|
| 3,918,896 | 11/1975 | Kalopissis et al. | 564/442 |
| 3,978,061 | 8/1976 | Kalopissis et al. | 564/367 |
| 3,979,262 | 9/1976 | Hunziker | 435/28 |
| 4,065,255 | 12/1977 | Andrillon et al. | 8/412 |
| 4,330,291 | 5/1982 | Bugaut et al. | 8/406 |
| 4,672,029 | 6/1987 | Washburn et al. | 435/28 |

FOREIGN PATENT DOCUMENTS

| | | |
|---|---|---|
| 0103784 | 3/1984 | European Pat. Off. . |
| 3037342 | 7/1981 | Fed. Rep. of Germany . |
| 0001896 | 1/1981 | Japan ................................ 435/28 |
| 132225 | 6/1975 | Norway . |
| 2069498 | 8/1981 | United Kingdom . |
| 8001081 | 5/1980 | World Int. Prop. O. . |

OTHER PUBLICATIONS

J. Org. Chem. Band 40, Nr. 1, 1975, Seiten 77–81.
Patrick, T. B. et al, *Synthesis of Fluoroaromatic Amines* J. Org. Chem, vol. 39, No. 12 (1974) pp. 1759–1761.
Galiani, G. et al *Horseradish Peroxidase-Catalyzed Oxidation of Tertiary Amines with Hydrogen Peroxide*, J.C.S. Perkin Trans. I, vol. 5 (1978) pp. 456–460.

*Primary Examiner*—Glennon H. Hollrah
*Assistant Examiner*—Kristina Lynne Konstas
*Attorney, Agent, or Firm*—Felfe & Lynch

[57] ABSTRACT

Fluorinated aniline derivatives of the general formula I are described

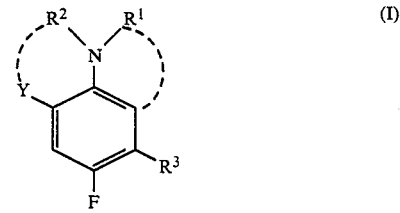

in which $R^1$ represents H or $(CH_2)_n$-X, n is a whole number from 1 to 3, X is H, OH, $NH_2$, $CH_3CONH$, $CH_3SO_2NH$, $SO_3H$ or $ArSO_3H$, Ar is optionally substituted arylene radical, $R^1$ is alternatively also a $—(CH_2)_3—$ group, which is bonded to the free o-position next to the N-atom, Y is H, —O—, —NH—, —S— or a C—C single bond, $R^2$, in the event that Y=H, is the same as or different from $R^1$ and means one of the radicals shown for $R^1$, and in the event that Y is a C—C single bond or —O—, —NH— or —S—, is an alkylene group having 1 to 3 carbon atoms linked with Y, and $R^3$=H, alkyl having 1 to 3 carbon atoms, $OCH_3$, $CH_3CONH$, $CO_2H$ or $SO_3H$.

The compounds of formula I form as coupling components together with the conventional color couplers a very sensitive chromogenic system which is suitable for the analytical determination of oxidizing substances, for example for the determination of $H_2O_2$ and POD in body fluids.

4 Claims, 2 Drawing Sheets

FLUORINATED ANILINE DERIVATIVES AND THEIR USE

This is a continuation of application Ser. No. 720,583 filed on Apr. 8, 1985, now abandoned.

The invention concerns fluorinated aniline derivatives and their use as coupling components in oxidative chromogenic reactions.

The oxidative color coupling (Emerson-Trinder reaction) of phenols or anilines with suitable coupling partners such as for example with 4-aminoantipyrine (4-AAP) or with methylbenzthiazolon-hydrazone (MBTH) can serve for the detection and for the determination of the oxidation agent used for the color coupling. This reaction can be employed as the basis for chemical diagnostic processes in enzymatic analysis or in other fields, e.g. for the determination of glucose, uric acid or cholesterine in body fluids by the determination of the hydrogen peroxide which is formed in the oxidation of these substances with enzymes such as glucose oxidase, uricase, and cholinesterase, for substrate and-/or peroxidase determination with hydrogen peroxide as the oxidizing agent, or also for the determination of peroxides, such as for example lipid peroxides in body fluids (cf. e.g. DE-OS 30 37 342). An important prerequisite for such methods of determination is a high sensitivity, i.e. the formation of dyes with a high extinction coefficient and with a high yield. This is especially important for example in clinical chemical diagnosis during the determination of substances which are only present in body fluids in small amounts, since determination problems caused, for example, the phrase by small amounts of serum components can be largely excluded. Similarly there is also a need in other fields, e.g. in immunology, where peroxidase is often used a labelling enzyme, for sensitive chromogenic systems.

It is known that in the oxidative coupling of phenols with coupling partners suitable for color formation, such as for example with 4-aminoantipyrine (4-AAP) or methylbenzthiazolonhydrazone (MBTH), the color yield based on the amount of the oxidizing agent can be increased when chlorinated or brominated phenols are inserted in the 4-position in the coupling reaction. This effect is based on the fact that in the chromogenic reaction using halogenized phenols there is a 2-electron oxidation process whereas the unsubstituted phenols in the 4-position are converted in a 4-electron oxidation process into the color compounds (cf. e.g. the Japanese patent publication 9821/79). The sensitivity for the determination of oxidation agents, such as for example $Fe^{3+}$ or enzymatically formed $H_2O_2$, is thus doubled when 4-halogenphenols are used in the color formation reaction.

In contrast to the halogenphenols, aniline derivatives which are substituted in the 4-position with chlorine or bromine show no or only a slight color formation during oxidative color coupling with 4-AAP or with MBTH (cf. J. Org. Chem. 3, (1938), 153; Analytical Chemistry 33, (1961), 722), whereas the compounds substituted with hydrogen which are however otherwise analogous supply as a rule, especially in the neutral to weak acidic pH range, dyes having higher extinction coefficients and longer-wave absorption maxima than the phenols. Even with N-substituted anilines, which are substituted in the o- or the p-position by a lower alkyl group, no satisfactory results are attained with respect to sensitivity and color stability (fc. DE-AS 28 33 612). The enzymatic oxidation of 4-fluoroaniline with the formation of a red benzoquinone-di-(p-fluoroanil) dye also proceeds very incompletely (cf. Inorganic Chemistry, published by G. L. Eichhorn, Elsevier, Amsterdam, 1973, vol. 1 and vol. 2, page 1000).

The use of 4-fluoroaniline and other fluorine derivatives of aniline has been adduced for the determination of hydrogen peroxide, e.g. in the enzymatic oxidation of organic substances (cf. PCT application WO 80/01081; Clinical Chemistry 28, (1982), No. 2, page 1962); but these processes are not based on an oxidative color coupling reaction but the fluorine ions released during the dissociation of a C—F bond catalysed by peroxide are measured electrometrically on an electrode which is selective for fluorine ions.

Therefore, there has been no shortage of attempts to develop new sensitive chromogenic systems for the determination of oxidation agents, such as for example hydrogen peroxide and peroxidase (POD). For example leuco dyes which can be oxidized in a 2-electron process with $H_2O_2$/POD to form color compounds have been proposed. But these leuco dyes often have the disadvantage as compared with the two-component systems that they are unstable against atmospheric oxygen or are only poor substrates of the peroxidase. During oxidative color coupling the developments led to improved aniline coupling components, wherein the increase in sensitivity was usually achieved by variation of the substituents on aniline nitrogen or on the C-3 atom (cf. e.g. DE-OS 30 37342; DE-AS 28 33 612).

It is therefore the object of the current invention to provide new aniline derivatives which lead during oxidative color coupling to dyes with higher absorbance and color stability and with a high yield, and which therefore form a sensitive chromogenic system for oxidative color coupling. This object is solved by the present invention.

The subject of the invention is provided by fluorinated aniline derivatives of the general formula

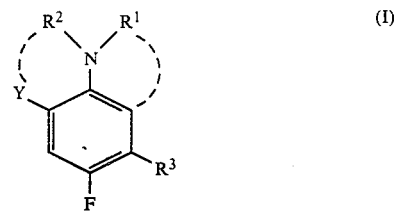

in which $R^1$ represents H or $(CH_2)_n$—X, n represents a whole number from 1 to 3, X represents $H, OH, NH_2, CH_3CONH, CH_3SO_2NH, SO_3H$ or Ar-$SO_3H$, Ar is an optionally substituted arylene radical, $R^1$ is alternatively also a —$(CH_2)_3$— group, which is linked at the free o-position next to the N-atom, Y is H,—O—,—NH—,—S—, or a C—C single bond, $R^2$, in the event that Y=H, is equal to or different from $R^1$ and represents a radical cited for $R^1$, and in the event that Y is a C—C—single bond or is —O—,—NH— or —S—, is an alkylene radical having 1 to 3 carbon atoms linked with Y, and $R^3$ is H, alkyl with 1 to 3 carbon atoms, $OCH_3, CH_3CONH, CO_2H$ or $SO_3H$.

The radical Ar can be substituted or preferably unsubstituted and is for example 1,4-naphthylene and especially 1,4-phenylene; a substituted Ar radical can have one or more, preferably one or two substituents, such as for example alkyl with 1 to 3 carbon atoms, OH,OCH₃ and/or halogen in particular chlorine.

$R^2$ in its meaning of alkylene is methylene, ethylene or trimethylene, and for Y in the meaning of the C—C single bond is preferably ethylene or trimethylene.

An alkyl radical with 1 to 3 carbon atoms is a methyl-, ethyl-, propyl-, or isopropyl radical.

Especially preferred compounds of formula I are N-(2-acetamidoethyl)-N-ethyl-4-fluoro-3-methyl-aniline (F-EMAE), N-ethyl-N-(4-fluoro-3-methyl-phenyl)-2-aminoethanesulfonic acid (F-EST), N-ethyl-N-(2-hydroxyethyl)-4-fluoro-3-methylaniline (F-EHT), 9-fluoro-julolidine, 9-fluoro-8-methyljulolidine and (6-fluoro-1,2,3,4-tetrahydroquinoline)-N-propanesulfonic acid (F-THC-PS).

It has been found that the fluorinated aniline derivatives of the general formula I, during oxidative color coupling with $H_2O_2$/POD and with a suitable coupling partner, such as for example 4-amino-antipyrine (4-AAP), 4,4'-diaminoantipyrine (4,4'-DAAP) or with sulfonated methylbenzthiazolonehydrazone (SMBTH), show a sensitivity which is almost twice that of the non-fluorinated analogues; the dyes which are produced during the coupling are the same. This result must be regarded as very surprising, because as we have mentioned above, it was previously known from the prior art that aniline derivatives substituted in the 4-position in contrast to their analogues which are not substituted in the 4-position show no color formation or a lower color formation during oxidative color coupling (cf. also FIG. 1).

In the table below the extinction coefficients measured at λ max. ($cm^2/\mu$ mol $H_2O_2$) of chromogenic systems oxidized with $H_2O_2$/POD, which contain the usual aniline coupling components and a color coupler, and the extinction coefficients of otherwise identical chromogenic systems, which however contain a fluorinated analogous aniline derivative according to the present invention instead of the usual aniline coupling components, are compared. 4-aminoantipyrine (4-AAP), 4,4'-diaminoantipyrine (4,4'-DAAP) and sulfonated methylbenzthiazolonehydrazone (SMBTH) were used as the color couplers. The cited quotient $\epsilon_F/\epsilon_H$ from the extinction coefficients of the oxidized chromogenic system with fluorinated coupling component ($\epsilon_F$) and of that with the non-fluorinated compound ($\epsilon_H$) is demonstrating the increase in the color yield when using the fluorinated coupling component.

The coupling reaction is carried out in the manner known per se (cf. for example DE-AS 28 33 612); preferably at room temperature, for which a ratio of the coupling component/color coupler of more than 5 has been found to be especially expedient. The pH-values are preferably in the neutral to weakly acidic range. Table I is based on the following values (concentrations in the reaction mixture):

TABLE I

| Potassium-phosphate buffer: | 0.1 mol/l |
|---|---|
| aniline coupling component: | 3 × 10⁻¹ mMol/l |
| color coupler: | 3 × 10⁻² mMol/l |
| hydrogen peroxide: | 1.5 × 10⁻² mMol/l |
| Peroxidase: | 120 U/l |

| Color coupler | Coupling Component | pH value | λ_max. | ε (cm²/μmolH₂O₂) | ε_F/ε_H |
|---|---|---|---|---|---|
| 4-AAP | EMAE | | 552 | 16.3 | |
| | F-EMAE | 5.5 | 552 | 29.8 | 1.83 |
| | EST | | 552 | 17.0 | |
| | F-EST | 5.5 | 552 | 30.5 | 1.8 |
| | EHT⁽¹⁾ | | 550 | 16.3 | |
| | F-EHT⁽¹⁾ | 5.5 | 548 | 29.2 | 1.79 |
| | F-THC-PS⁽²⁾ | 5.5 | 555 | 28.9 | — |
| | Julolidine⁽³⁾ | | 487 | 7.3 | |
| | 9-F-Julolide⁽³⁾ | 5.5 | 546 | 22.8 | — |
| | Julolidine⁽³⁾ | | 544 | 4.7 | |
| | 9-F-Julolide⁽³⁾ | 7.0 | 547 | 20.3 | 4.3 |
| 4,4'-DAAP | EMAE | | 554 | 17.8 | |
| | F-EMAE | 5.5 | 554 | 32.7 | 1.84 |
| | EST | | 554 | 19.2 | |
| | F-EST | 5.5 | 554 | 33.8 | 1.76 |
| S-MBTH | EMAE | | 570 | 30.4 | |
| | F-EMAE | 5.5 | 570 | 49.8 | 1.64 |
| | EST | | 580 | 30.2 | |
| | F-EST | 5.5 | 580 | 42.0 | 1.4 |
| | 9-F-8-Methyl-julolidine | 5.5 | 525 | 50.6 | — |
| | F-THC-PS | 5.5 | 565 | 51.5 | — |

⁽¹⁾Reaction mixture still contains 0.15 g/l triton X-100
⁽²⁾The concentration of the coupling component in this test is 6 × 10⁻² mMol/l
⁽³⁾reaction mixture still contains 1 g/l triton X-100

From Table I it can be seen that using the inventive aniline derivatives fluorinated in the 4-position under otherwise identical conditions, substantially higher extinction values (by the factor of 1.4 to 1.84) are obtained; thus using the compounds according to the invention, coupling components are made available whose use together with the conventional color couplers produces a very sensitive chromogenic system for oxidative color coupling.

Therefore the subject of the invention is also the use of the compounds according to the invention of the general formula I as coupling components in oxidative color formation reactions, especially for the determination of $H_2O_2$ and of POD, as well as an agent for the analytical determination of oxidizing substances, especially $H_2O_2$, by means of oxidative color coupling which is characterized in that it contains as coupling component a compound according to the invention having the formula I.

The color couplers generally used for such color coupling reactions can be used as the color couplers; preferred are 4-amino-antipyrine (4-AAP), 4,4'-diamino-antipyrine (4,4'-DAAP) or sulfonated methyl-benzthiazolonehydrazone (SMBTH).

The inventive compounds of formula I can be prepared according to the synthesis methods known per se, for example according to a process known for the corresponding aniline derivatives unsubstituted in the 4-position (cf. for example European Patent 0007787; DE-AS 28 56 487; DE-OS 30 03 490) while making use of a correspondingly fluorinated initial product.

FIG. 1 shows the comparison of the chromogenic system EMAE/4-aminoantipyrine and halogen-EMAE/4-aminoantipyrine during color formation by oxidation with $H_2O_2$/POD. The concentrations in the reaction mixture correspond to the values shown above for Table I; in addition, the reaction mixture contains 0.5 g/l of triton X-100. The reaction was started by the addition of peroxidase. Measuring wave length is 550 nm. FIG. 1 makes clear the surprisingly and substantially higher sensitivity when using the inventive aniline derivatives fluorinated in the 4-position against otherwise identical chromogenous systems which contain an unsubstituted aniline derivative or a derivative substituted by chlorine or bromine.

A special advantage of the use of fluorinated coupling components is observed in the case of julolidine. If the oxidative coupling of 4-aminoantipyrine is carried out with julolidine at pH 5.5, a dye is obtained whose $\lambda_{max}$ is only 487 nm, whereas when using 9-fluorojulolidine, a dye is obtained with a $\lambda_{max}$ in the range of 550 nm (546 nm) (cf. FIG. 2).

EXAMPLES

Example 1

N-(2-acetamidoethyl)-N-ethyl-4-fluoro-3-methyl-aniline (F-EMAE)

(a) N-ethyl-4-fluoro-3-methyl-aniline

At room temperature for a period of 45 minutes a solution of 15.05 g (0.09 mol) of N-acetyl-4-fluoro-3-methyl-aniline in 80 ml THF (abs.) is dropped to a suspension of 4.55 g (0.12 mol) lithium-aluminum-hydride in 50 ml of tetrahydrofurane (abs.) and thereafter refluxed for 2 hours. The reaction mixture is then evaporated.

After addition of 50 ml ether the excess LiAlH$_4$ is destroyed by dropwise addition of water, dried with sodium sulfate and filtered off with suction. The filter residue is washed with ether, the filtrate is concentrated by evaporation and distilled in a Kugelrohr-apparatus (oven temperature 155° C.) at 18 torr.

The yield is 12.5 g=91% of theoretical.

$^1$H-NMR (CDCl$_3$): $\delta$1.16 (t, J=7 Hz, 3H); 2.15 (d, J=2 Hz, 3H); 3.0 (dq, J=7 Hz; J=7 Hz, 2H); 5.31 (s br., 1H); 6.39 (ddd, J=9; 3.5 and 3.5 Hz, 1H, H-6); 6.45 (dd, J=6, 5 Hz, J=3.5 Hz, 1H, H-2); 6.88 ppm (dd, J=9 Hz, J=9 Hz, 1H, H-5).

Element analysis: calc. F 12.40 (C$_9$H$_{12}$FN, 153,2) found F 11.97.

(b) N-(2-acetamidoethyl)-N-ethyl-4-fluoro-3-methyl-aniline 7.66 g (50 mMol) N-ethyl-4-fluoro-3-methyl-aniline and 4.68 g (55 mMol) N-acetylaziridine are refluxed in 100 ml methanol (abs.) for 15 hours. Then the reaction mixture is evaporated on a rotary evaporator and the residue is digested with diisopropylether. The solid thus obtained is filtered with suction, washed with diisopropylether and dried.

Yield: 4.65 g=39% of th.

m.p. =88° C.

$^1$H-NMR (DMSO-D$_6$): $\delta$=1.04 (t, J=7 Hz, 3H); 1.80 (s, 3H); 2.17 (d, J=2 Hz, 3H); 3,2 (m, 4H); 3,29 (q, J=7 Hz, 2H); 6.37–6.70 (m, 2H); 6.87 (dd, J=9 Hz; J=9 Hz, 1H); 7.9 ppm (s br, 1H).

Element analysis: calc. C 65.52 H 8.04 F 7.97 N 11.76 (C$_{13}$H$_{19}$FN$_2$O, 238.31) found C 65.74 H 8.31 F 8.22 N 11.88.

In an analogous manner starting from N-acetyl-4-(chloro or bromo)-3-methyl-aniline it is possible to obtain the comparable compounds Cl-EMAE and Br-EMAE.

Example 2

N-ethyl-N-(4-fluoro-3-methyl-phenyl)-2-aminoethane sulfonate acid (F-EST), sodium salt A mixture of 12.25 g (80 mMol) N-ethyl-4-fluoro-3-methyl-aniline (example 1a), 18.57 g (88 mMol) 2-bromoethanesulfonic-acid-sodium salt, 100 mg potassium iodide, 29.7 g (160 mMol) tributylamine and 20 ml DMF is heated for 12 hours at 170° C. bath temperature. During cooling 8 ml 10N NaOH are added at about 90° C. After the addition of a little acetone, nonreacted bromineethanesulfonic acid is precipitated in the refrigerator and separated by filtration. The residue after the concentration of the filtrate on the rotary evaporator is recrystallized from butanol.

Yield: 5,3 g=23% of th.

$^1$H-NMR (DMSO-D$_6$): $\delta$=1.06 (t, J=7 Hz, 3H); 2.19 (d, J=2 Hz, 3H); 2.69 ("t", J=8 Hz, 2H); 3.30 (q, J=7 Hz, 2H); 3.52 ("t", J=8 Hz, 2H); 6.50 (ddd, J=9, 3.5 and 3.5 Hz, 1H, H-6); 6.57 (dd, J=6,5 Hz, J=6,5 Hz, 1H, H-2), 6.93 ppm (dd, J=9 Hz, J=9 Hz, 1H, H-5).

Element analysis: calc. C 46.64 H 5.34 F 6.71 N 4.94 S 11.32 Na 8.19 (C$_{11}$H$_{15}$FNNaSO$_3$, 283,3) found C 44.22 H 5.20 F 5,92 N 4.70 S 11.00 Na 8.15.

Example 3

N-ethyl-N-(4-sulfophenyl-methyl)-4-fluoro-3-methyl-aniline, sodium salt

A mixture of 1,53 g (10 mMol) N-ethyl-4-fluoro-3-methyl-aniline 2,73 g (10 mMol) 4-bromomethyl-benzenesulfonic acid sodium salt (made by NBS brominating of 4-toluene sulfonic acid chloride and subsequent treatment with 1 equivalent NaOH) and 2.8 ml triethylamine in 90 ml DMF is refluxed for 6 hours. During cooling 2 ml 10N sodium hydroxide is added and evaporated under reduced pressure. The product obtained from the residue by recrystallization from n-butanol is filtered by suction, washed in ether and dried.

Yield: 0.1 g.

$^1$H-NMR (DMSO-D$_6$): $\delta$=1.09 (t, J=7 Hz, 3H); 2.13 (d, J=2 Hz, 3H); 3.38 (q, J=7 Hz, 2H); 4.42 (s, 2H); 6.3–6,6 (m, 2H); 6.83 (dd, J=9 Hz; J=9 Hz, 1H); 7.15 and 7.53 ppm (AA'BB'-System, J=9 Hz, 4H).

Example 4

N-ethyl-N-(2-dydroxy ethyl)-4-fluoro-3-methyl-aniline (F-EHT)

7.66 g (0,05 Mol)N-ethyl-4-fluoro-3-methylaniline, 20.1 g (0.25 Mol) 2-chloroethanol and 15 g (0.15 Mol) calciumcarbonate in a mixture of 40 ml dioxane and 20 ml water are refluxed for 50 hours. After cooling water is added to the reaction mixture and extracted with ethylacetate. The organic phase is washed repeatedly with water, dried with sodium sulfate and the residue obtained after evaporation is distilled in the Kugelrohr-apparatus at 0.1 torr with an oven temperature of 145° C.

Yield: 5.3 g=54% of th.

$^1$H-NMR (DMSO-D$_6$): $\delta$=1.06 (t, J=7 Hz, 3H); 2.17 (d, J=2 Hz, 3H); 3,2–3.35 (m, 4H); 3.50 (q, J=7 Hz, 2H); 4.54 (t, J=5 Hz, 1H; OH); 6.44 (ddd, J=9; 3.5 and 3.5 Hz, 1H, H-6); 6.51 (dd, J=6,5 Hz, J=3.5 Hz, 1H, H-2); 6.85 ppm (dd, J=9 Hz, J=9 Hz, 1H, H-5).

Element analysis calc. C 66.98 H 8.18 F 9.63 N 7.10 (C$_{11}$H$_{16}$FNO, 197,25) found C 66.44 H 8.25 F 9.66 N 7.61.

Example 5

3-(6-fluoro-1,2,3,4-tetrahydro-1-quinolyl)-propanesulfonic acid

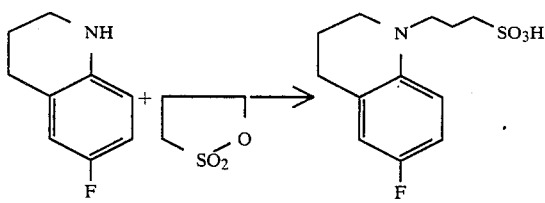

To 6,05 g (40 mMol) 6-fluoro-1,2,3,4-tetrahydroquinoline in 20 ml acetone, 5.9 g (48 mMol) of propane sultone dissolved in 20 ml acetone are added dropwise for a period of 40 minutes at 50° to 60° C. After 24 hours of refluxing and again after 48 hours a further 5.9 g of propane sultone are added. After a total of 60 hours of refluxing, the reaction mixture is concentrated by evaporation and the volatile components are removed in high vacuum (0.01 torr) by heating to about 150° C. The residue is recrystallized from 115 ml methanol.

Yield: 4.1 g=38% of th.
m.p. 233° to 236° C.
MS (trimethylsilylized derivative): m/e 345 (M+).

Example 6

9-fluorojulolidine-hydrochloride 55.5 g (0.5 mol) 4-fluoroaniline and 472.2 g (3 mol) 1-bromo-3-chloropropane are refluxed for 21 hours. During cooling, at 50° C. 45 ml concentrated hydrochloric acid and 375 ml water are added and the excessive bromochloro-propane is removed by water-steam distillation. The distillation residue is adjusted to alkaline with 33% sodium hydroxide solution and is twice extracted using chloroform. The combined organic phases are washed with water, dried over sodium sulfate and distilled of solvent on a rotary evaporator. The purification of the residue thus obtained is carried out by fractionated distillation (b.p. 110-113 C/0.4 torr).

Yield: 27.9 g =29% of th.

956 mg (4 mMol/l) 9-fluorojulolidine in 5 ml acetone are reacted with 497 μl (6 mMol) hydrochloric acid 37% in 5 ml acetone with ice-cooling. The precipitated product is filtered with suction, washed with acetone and recrysatallized from isopropanol.

m.p. 221°–224° C.

$^1$H-NMR (DMSO-D$_6$): δ=2.11 (quintette, J=7 Hz, 4H); 2.84 (t, J=7 Hz, 4H); 3.29 ("t", 4H); 5.8 (s.br., 1H); 6.86 ppm (d, J=9 Hz, 2H).

Element analysis: calc. C 63.30 H 6.64 N 6.15 (C$_{12}$H$_{15}$ClFN, 227,71) found C 62.89 H 6.62 N 6.09.

Figure 2:
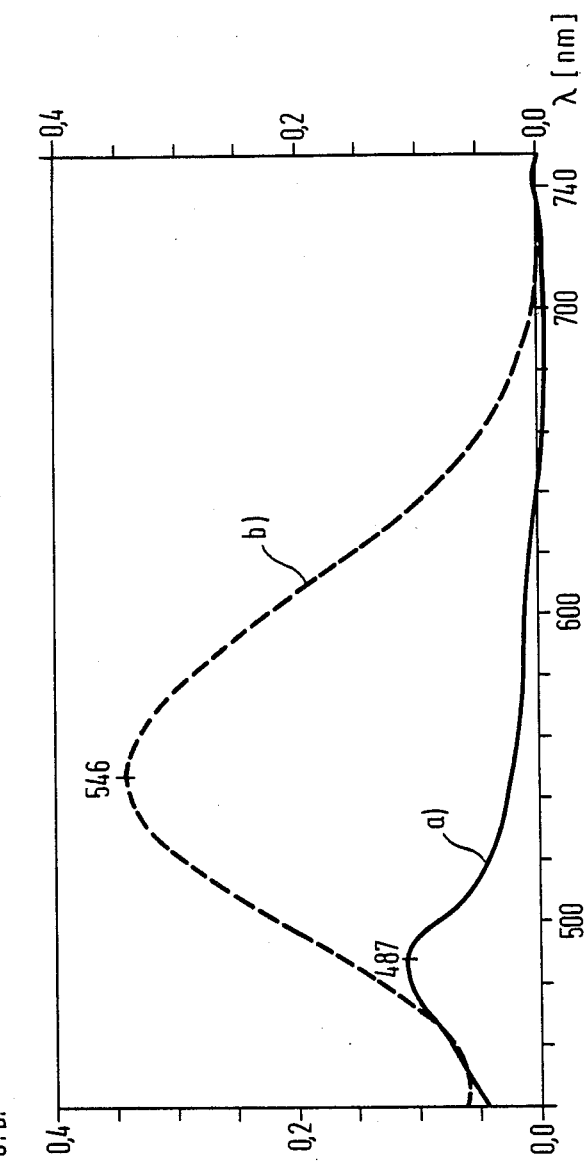

FIG. 2 shows the optical density of the formed dyes at pH 5.5 obtained after coupling of 4-amino-antipyrine with julolidine (curve a) and with 9-fluoro-julolidine (curve b).

The concentrations in the reaction mixture correspond to the values given in table 1. The reaction mixture contains additionally 1 g/l superfactant agent (triton X 100).

Example 7

9-fluoro-8-methyljulolidine 11.25 g (9.99 mol) 4-fluoro-3-methylaniline and 85 g (0.54 mol) 1-bromo-3-chloropropane are refluxed for 24 hours. After cooling of the reaction mixture to about 50° C., 10 ml concentrated hydrochloric acid and 70 ml water are added and bromochloropropane is removed by water-steam distillation. The distillation residue is alkalized with 33% sodium hydroxide solution and twice extracted using chloroform. After drying, the organic phase is evaporated. A part of the residue is purified by liquid-solid chromatography over silica gel (elution with chloroform→methanol).

MS: m/e=205 (M+).

We claim:

1. A fluorinated aniline derivative of the formula

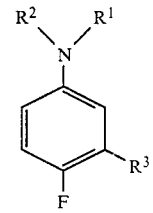

in which
R$^1$ represents (CH$_2$)$_n$—X wherein n represents a whole number from 1 to 3 and X is H, OH, NH$_2$ or CH$_3$CONH,
R$^2$ represents (CH$_2$)$_n$—X wherein n represents a whole number from 1 to 3 and X is OH, NH$_2$ or CH$_3$CONH, and
R$^3$ represents H, alkyl having from 1 to 3 carbon atoms, OCH$_3$ or CH$_3$CONH.

2. A fluorinated aniline derivative according to claim 1 in which R$^2$ is different from R$^1$.

3. The fluorinated aniline derivative of claim 2 designated N-(2-acetamidoethyl)-N-ethyl-4-fluoro-3-methylaniline.

4. The fluorinated aniline derivative of claim 2 designated N-ethyl-N-(2-hydroxyethyl)-4-fluoro-3-methylaniline.

* * * * *